US009205081B2

(12) United States Patent
Toledano

(10) Patent No.: US 9,205,081 B2
(45) Date of Patent: Dec. 8, 2015

(54) COMBINATIONS OF OPIOD/TLR4 ANTAGONIST AND A CYCLOOXYGENASE (COX) INHIBITOR FOR USE IN THE TREATMENT OF PAIN

(71) Applicant: Annette Channa Toledano, North Miami, FL (US)

(72) Inventor: Annette Channa Toledano, North Miami, FL (US)

(73) Assignee: Allodynic Therapeutics, LLC, North Miami, FL (US)

( * ) Notice: Subject to any disclaimer, the term of this patent is extended or adjusted under 35 U.S.C. 154(b) by 0 days.

(21) Appl. No.: 13/841,100

(22) Filed: Mar. 15, 2013

(65) Prior Publication Data

US 2014/0275142 A1 Sep. 18, 2014

Related U.S. Application Data

(63) Continuation-in-part of application No. 12/824,367, filed on Jun. 28, 2010.

(60) Provisional application No. 61/343,489, filed on Apr. 29, 2010, provisional application No. 61/395,772, filed on May 17, 2010.

(51) Int. Cl.
*A61K 31/485* (2006.01)
*A61K 31/192* (2006.01)
*A61K 45/06* (2006.01)

(52) U.S. Cl.
CPC ............. *A61K 31/485* (2013.01); *A61K 31/192* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 6,541,478 | B1 | 4/2003 | O'Malley et al. |
| 6,716,449 | B2 | 4/2004 | Oshlack et al. |
| 2002/0058673 | A1 | 5/2002 | Kaiko et al. |
| 2003/0022926 | A1 | 1/2003 | Lavand'Homme |
| 2004/0024004 | A1* | 2/2004 | Sherman et al. ............. 514/282 |
| 2005/0038062 | A1 | 2/2005 | Burns et al. |
| 2007/0060500 | A1 | 3/2007 | Mickle et al. |
| 2007/0191350 | A1 | 8/2007 | Field et al. |
| 2007/0259939 | A1 | 11/2007 | Stebbing |
| 2010/0120812 | A1 | 5/2010 | Chapleo et al. |
| 2011/0251229 | A1 | 10/2011 | Watkins et al. |
| 2011/0269727 | A1 | 11/2011 | Toledano |

FOREIGN PATENT DOCUMENTS

WO 2012048294 A2 4/2012

OTHER PUBLICATIONS

Hersch et al., Narcotic receptor blockade and its effect on the analgesic response to placebo and ibuprofen after oral surgery, Oral Surgery, Oral Medicine, Oral Pathology, May 1993, vol. 75(5): 539-546.*
Younger et al., Fibromyalgia Symptoms are Reduced by Low-Dose Naltrexone: A Pilot Study, Pain Medicine. May 2009, vol. 10 Issue 4, p. 663-672.*
U.S. Appl. No. 13/837,099, filed Mar. 2013, Toledano.*
U.S. Appl. No. 13/851,267, filed Mar. 2013, Toledano.*
Hersh et al. 'Narcotic receptor blockade and its effect on the analgesic response to placebo and ibuprofen after oral surgery.' Oral Surgery, Oral Medicine, Oral Pathology. 1993, vol. 75, No. 5, pp. 539-546.
Kumar et al. 'Gabapentin in the management of pentazocine dependence: a potent analgesic-anticraving agent' J Assoc Physicians India. 2003, vol. 51, pp. 673-676.
International Search Report and Written Opinion of the International Searching Authority, PCT/US2014/025771, Aug. 26, 2014 (26 pages).
Office Action in related U.S. Appl. No. 13/837,099, filed Mar. 15, 2013, mailed Aug. 15, 2014.
Vining et al. 'Clinical Utility of Rapid Clonidine—naltrexone Detoxification for Opioid Abusers'. British Journal of Addiction. 1988, vol. 83, No. 5, pp. 567-575.
De Marinis et al. 'Headache in the use and withdrawal of opiates and other associated substances of abuse'. Headache: The Journal of Head and Face Pain. 1991, vol. 31, No. 3, pp. 159-163.
Younger et al. 'Fibromyalgia Symptoms Are Reduced by Low-Dose Naltrexone: A Pilot Study.' Pain Medicine, 2009, vol. 10, No. 4, pp. 663-672.
Way et al. 'Opioid Analgesics & Antagonists'. Basic and Clinical Pharmacology. 7th Edition, Appleton & Lange, pp. 496-515 (1998). **.
Serajuddin. 'Salt Formation to Improve Drug Solubility'. Advanced Drug Delivery Reviews. 2007, vol. 59, pp. 603-616.
Office Action in related U.S. Appl. No. 12/824,367, filed Jun. 28, 2010, dated Jul. 16, 2014.
Final Office Action in related U.S. Appl. No. 13/837,099, filed Mar. 15, 2013, mailed Jan. 8, 2015.
Notice of Allowance in related U.S. Appl. No. 13/837,099, filed Mar. 15, 2013, mailed Apr. 21, 2015.
Notice of Allowance in related U.S. Appl. No. 13/837,099, filed Mar. 15, 2013, mailed Jun. 9, 2015.
Non-Final Office Action in related U.S. Appl. No. 13/851,267, filed Mar. 27, 2013, mailed Jun. 9, 2015.
Non-Final Office Action in related U.S. Appl. No. 13/851,773, filed Mar. 27, 2013, mailed Jun. 9, 2015.
Hutchinson et al. (2008) "Non-stereoselective reversal of neuropathic pain by naloxone and naltrexone: involvement of toll-like receptor 4 (TLR4)," Eur. J. Neurosci. 28:20-29.

\* cited by examiner

*Primary Examiner* — Svetlana M Ivanova
(74) *Attorney, Agent, or Firm* — Lathrop & Gage LLP

(57) ABSTRACT

Disclosed are compositions for treatment of pain comprising a first compound and a second compound, the first compound is an opioid antagonist that treats pain by blocking Toll-like receptor 4 (TLR4) and the second compound is a cyclooxygenase (COX) inhibitor that enhances the pain treatment effect of the first compound. Examples of opioid antagonist include naltrexone and naloxone. Examples of cyclooxygenase inhibitors include ibuprofen, naproxen, meloxicam, diclofenac and meclofenamic acid, synergistic pharmaceutical compositions thereof, and their use in the treatment, prevention, and reversal of neuropathic pain and nociceptive pain with an allodynic component.

9 Claims, No Drawings

COMBINATIONS OF OPIOD/TLR4 ANTAGONIST AND A CYCLOOXYGENASE (COX) INHIBITOR FOR USE IN THE TREATMENT OF PAIN

CROSS-REFERENCE TO RELATED APPLICATIONS

This application is a continuation-in-part of U.S. application Ser. No. 12/824,367 filed Jun. 28, 2010, which claims the benefit of U.S. patent Provisional Application Ser. No. 61/343,489, entitled "Method for treating pain by a composition of naltrexone/clonidine at any dose combination" filed on Apr. 29, 2010 and Provisional Application Ser. No. 61/395,772 entitled "Compositions for treatment of pain, including but not exclusive to affect spinal pain (back pain), arthritic joint pain and migraine headache, pain of neuropathic and nociceptive origin" filed on May 17, 2010 the entire teachings of which are incorporated herein by reference.

FIELD OF INVENTION

This invention relates to combinations of an opioid/TLR4 antagonist and a cyclooxygenase (COX) inhibitor, particularly those that exhibit a synergistic effect for the treatment, prevention and reversal of pain.

BACKGROUND

It is well established in medical literature that treatments currently available for pain have limitations. Opioid drugs cause tolerance, dependence and side effects sufficiently serious to prompt recent action by the FDA to further restrict the drugs. Newly approved treatments, like the calcium channel alpha-2-delta ligands gabapentin and pregabalin and the serotonin and norepinephrine reuptake inhibitors milnacipran and duloxetine, require high doses to show nominal effectiveness, have a high dropout rate and carry many side effects.

This invention is a novel approach for the treatment of pain. It is directed to the treatment of neuropathic and nociceptive pain with an allodynic component. One component of the combination is directed to reducing neuropathic pain and the allodynic component associated with nociceptive pain and the other component address nociceptive pain. Specific combination of drugs and the dosage needed to create that effect is the subject of the instant invention.

The unifying theory explaining neuropathic pain is the understanding that TLR4 are activated endogenously and trigger a pro-inflammatory cascade. That cascade is interrupted and in most cases eliminated by treatment using the systemic administration of an opioid/TLR4 antagonist, particularly naltrexone, or a pharmaceutically acceptable salt, thereof.

A cyclooxygenase (COX) inhibitor particularly ibuprofen, or a pharmaceutically acceptable salt thereof, enhances the pain relief action of the opioid/TLR4 antagonist naltrexone. A specific synergistic dose range of the combination is herein presented.

In a dose finding study the combination of the opioid/TLR4 antagonist, naltrexone and the cyclooxygenase (COX) inhibitor ibuprofen, acted synergistically, whether administered separately, one right after the other, or administered in combination.

Various μ-opioid receptor ligands have been tested and were found to also possess action as agonists or antagonists of Toll-like receptor 4 (TLR4). Toll-like receptors, found in the glia, are a class of receptors that play a key role in the innate immune system. They recognize pathogen-associated molecular patterns (PAMPs) such as lipopolysaccharide (LPS) that are expressed on infectious agents, and mediate the production of cytokines necessary for the development of effective immunity. Opioid agonists such as morphine act as TLR4 agonists, while opioid antagonists such as naloxone and naltrexone were found to be TLR4 antagonists. Activation of TLR4 by opioid agonists such as morphine leads to downstream release of inflammatory modulators including TNF-α and interleukin-1. Constant low-level release of these modulators is thought to reduce the efficacy of opioid drug treatment with time and to be involved in both the development of tolerance to opioid analgesic drugs and in the emergence of side effects such as hyperalgesia and allodynia which can become problems following extended use of opioid drugs.

Accordingly, the instant invention relates to μ-opioid receptor ligand as ligands of TLR4 as well and contemplates that allodynia is caused by activation of TLR4. Blockage of TLR4 accordingly will eliminate allodynia.

The best known opioid receptor antagonists are naloxone and naltrexone. Naltrexone is an opioid receptor antagonist used primarily in the management of alcohol dependence and opioid dependence. A dose of 50-300 mg once daily is recommended for most patients. Naloxone is an opioid inverse agonist: it is a drug used to counter the effects of opiate overdose.

Low dose naltrexone describes the off label use of naltrexone at doses less than 10 mg per day for indications other than chemical dependency or intoxication.

It has been suggested in the literature that low dose naltrexone exerts the opposite effect of naltrexone in full dose. While the full dose naltrexone blocks the opiate system, the low dose naltrexone promotes the production of endorphins by the mechanism of up regulation caused by partial opiate receptor blockage. The beneficial effect of naltrexone was attributed to the increase in endorphins. The beneficial effect of low dose naltrexone can be further explained by its antagonism of TLR4.

Other opioid receptor antagonists used in clinical or scientific practice which also can be used for the treatment of pain include but are not limited to the following: naloxone, nalmefene, norbinaltorphimine, nalorphine, methylnaltrexone, samidorphan, cyprodime, naltrindole, amentoflavone, naltriben, norbinaltorphimine, and the naltrexone metabolite 6-β-naltrexol.

Our understanding of pathological pain has primarily revolved around neuronal mechanisms. However, neighboring glia, were TLL4 reside, including astrocytes and microglia; have recently been recognized as powerful modulators of pain.

Studies show that TLRs can be activated not only by well-known "non-self" molecular signals but also by endogenous signals (IL-1β, TNFα, IL-6 and NO) produced during chronic neuropathic pain states. Fibronectin, an endogenous TLR4 ligand that is produced in response to tissue injury, leads to an up regulation of the purinoceptor P2X4, which is expressed exclusively on microglia.

Several opioid antagonist drugs were found to act as antagonists for TLR4, including naloxone and naltrexone. However it was found that not only the "normal" (−) enantiomers, but also the "unnatural" (+) enantiomers of these drugs acted as TLR4 antagonists. The unnatural enantiomers of the opioid antagonists, (+)-naltrexone and (+)-naloxone, dextro-naltrexone and dextro-naloxone, have been discovered to act as selective antagonists of TLR4. Since (+)-naloxone and (+)-naltrexone lack affinity for opioid receptors, they do not block the effects of opioid analgesic drugs, and so can be used to counteract the TLR4-mediated side effects of opioid agonists without affecting analgesia. (+)-Naloxone was also found to be neuroprotective, and both (+)-naloxone and (+)-naltrexone are effective in their own right at treating symptoms of neuropathic pain in animal models.

Most nonsteroidal anti-inflammatory drugs (NSAIDs) act as nonselective inhibitors of the enzyme cyclooxygenase (COX), inhibiting both the cyclooxygenase-1 (COX-1) and cyclooxygenase-2 (COX-2) isoenzymes. This inhibition is competitively reversible (albeit at varying degrees of reversibility). COX catalyzes the formation of prostaglandins and thromboxane from arachidonic acid. Prostaglandins act as messenger molecules in the process of inflammation. This mechanism of action was elucidated by John Vane (1927-2004), who received a Nobel Prize for his work. NSAIDs are usually indicated for the treatment of acute or chronic conditions where pain and inflammation are present Ibuprofen is a nonsteroidal anti-inflammatory drug (NSAID) it is used primarily for fever, pain, dysmenorrhea and inflammatory diseases such as rheumatoid arthritis; it is also used for pericarditis. Ibuprofen is a 'core' medicine in the World Health Organization's Model List of Essential Medicines necessary to meet the minimum medical needs of a basic healthcare system.

Ibuprofen enhances the pain treatment effect of naltrexone by inhibiting the enzyme cyclooxygenase (COX), which converts arachidonic acid to prostaglandin H2 (PGH2). PGH2, in turn, is converted by other enzymes to several other prostaglandins, which are mediators of pain, inflammation, and fever.

Nociceptive pain is caused by stimulation of peripheral nerve fibers that respond only to stimuli approaching or exceeding harmful intensity (nociceptors), and may be classified according to the mode of noxious stimulation. Deep somatic pain is initiated by stimulation of nociceptors in ligaments, tendons, bones, blood vessels, fasciae and muscles, and is dull, aching, poorly localized pain. Examples include sprains and broken bones.

Allodynia is a clinical feature of many painful conditions, such as back pain, chronic pain, neuropathic pain, diabetic neuropathic pain, trigeminal neuralgia pain, phantom limb pain, complex regional pain syndrome pain, acute herpetic pain, post herpetic pain, causalgia pain, idiopathic pain, inflammatory pain, cancer pain, postoperative pain, fibromyalgia pain, headache pain, migraine pain, allodynia pain, vulvodynia pain, interstitial cystitis pain, irritable bowel syndrome (IBS), arthritic joint pain and tendinitis. It becomes apparent that allodynia plays a role in every kind of pain.

The unifying theory of allodynia, or "memory pain", as allodynia may be described in lay terms, is the understanding that TLR4 are activated endogenously and trigger a pro-inflammatory cascade. That cascade is interrupted by the opioid/TLR4 antagonist drugs as claimed by the instant invention. Additionally, TLR4 antagonism can play a role in improving nociceptive pain as well by affecting the allodynic component of nociceptive pain.

Based upon this, the instant invention first teaches the use of an opioid/TLR4 antagonist, particularly naltrexone for its antagonism of the TLR4 and blocking release of inflammatory modulators. Secondly, the invention teaches use of a cyclooxygenase inhibitor, particularly ibuprofen, for its action on nociception and its anti-inflammatory action. The invention teaches that the combination is synergy as far as the effect on pain treatment.

The invention contemplates several forms of opioid antagonist selected from a group consisting of naltrexone, naloxone, nalmefene, norbinaltorphimine, nalorphine, methylnaltrexone, samidorphan, cyprodime, naltrindole, amentoflavone, naltriben, norbinaltorphimine, and metabolite 6-β-naltrexol and metabolites and pro drugs thereof, including all enantiomeric and epimeric forms as well as the appropriate mixtures thereof, or pharmaceutically acceptable salts or solvates of any thereof.

Nonsteroidal anti-inflammatory drug can be classified based on their chemical structure or mechanism of action. Older NSAIDs were known long before their mechanism of action was elucidated and were for this reason classified by chemical structure or origin. Newer substances are more often classified by mechanism of action.

The invention contemplates several forms of NSAID's selected from groups consisting of Salicylates: Aspirin Diflunisal, Salsalate. Propionic acid derivatives: Ibuprofen, Dexibuprofen, Naproxen, Fenoprofen, Ketoprofen, Dexketoprofen, Flurbiprofen, Oxaprozin, Loxoprofen. Acetic acid derivatives: Indomethacin, Tolmetin, Sulindac, Etodolac, Ketorolac, iclofenac, Nabumetone. Enolic acid (Oxicam) derivatives: Piroxicam, Meloxicam, Tenoxicam, Droxicam, Lornoxicam, Isoxicam. Fenamic acid derivatives: Mefenamic acid, Meclofenamic acid, Flufenamic acid, Tolfenamic acid. Selective COX-2 inhibitors: Celecoxib, Rofecoxib, Valdecoxib, Parecoxib, Lumiracoxib, Etoricoxib, Firocoxib, Sulphonanilides, Nimesulide, LOX (lipooxygenase) & COX 5-LOX/COX inhibitor: Licofelone, Lysine, clonixinate. Natural: Hyperforin, Figwort, Calcitriol (Vitamin D).

SUMMARY OF INVENTION

The instant invention is a synergistic combination product comprising a first compound and a second compound, where the first compound is an opioid antagonist that treats neuropathic pain by blocking receptor TLR4 and the second compound is a cyclooxygenase (COX) inhibitor that treats nociceptive pain by inhibiting cyclooxygenase, it enhances the pain treatment effect of the first compound. Another invention embodiment is a method for the treatment, prevention, and reversal of pain, neuropathic as well as nociceptive pain.

DESCRIPTION OF EMBODIMENTS

This invention provides a combination, comprising an opioid/TLR4 antagonist, and pharmaceutically acceptable salts or solvates of any thereof, and a cyclooxygenase inhibitor, and pharmaceutically acceptable salts or solvates of any thereof.

Another invention embodiment is a combination, comprising an opioid antagonist and a cyclooxygenase inhibitor. The opioid/TLR4 antagonist is selected from a group consisting of naltrexone, norbinaltorphimine, nalmefene, naloxone, nalorphine, methylnaltrexone, samidorphan, cyprodime, naltrindole, amentoflavone, naltriben, norbinaltorphimine, 6-β-naltrexol and metabolites thereof, including all enantiomeric and epimeric forms as well as the appropriate mixtures thereof, as well as pro drugs or metabolites thereof or pharmaceutically acceptable salts or solvates of any thereof.

Another invention embodiment is a combination, comprising an opioid antagonist and a cyclooxygenase inhibitor wherein, a cyclooxygenase inhibitor is selected from a group consisting of aspirin, diclofenac, difluinsal, etodolac, fenbufen, fenoprofen, flufenisal, flurbiprofen, ibuprofen, indomethacin, ketoprofen, ketorolac, meclofenamic acid, mefenamic acid, nabumetone, naproxen, oxaprozin, phenylbutazone, piroxicam, sulindac, tolmetin, zomepirac, and their pharmaceutically acceptable salts or solvates or pharmaceutically acceptable salts or solvates of any thereof.

Another invention embodiment is a combination, comprising an opioid antagonist and a cyclooxygenase inhibitor, the opioid antagonist/TLR4 is naltrexone as well as pro drugs and all enantiomeric and epimeric forms, specifically, (+)-naltrexone (dextro-naltrexone), as well as the appropriate mixtures thereof, or pharmaceutically acceptable salts or solvates of any thereof.

Another invention embodiment is a combination, comprising an opioid antagonist and a cyclooxygenase inhibitor, the opioid antagonist/TLR4 is naltrexone in a sustained release formulation, as well as pro drugs thereof or any enantiomeric and epimeric forms thereof, as well as the appropriate mixtures thereof, or pharmaceutically acceptable salts or solvates of any thereof.

Another invention embodiment is a combination, comprising an opioid antagonist and a cyclooxygenase inhibitor, the opioid antagonist/TLR4 is (+)-naltrexone (dextro-naltrexone), as well as pro drugs thereof or any enantiomeric and epimeric forms thereof, as well as the appropriate mixtures thereof, or pharmaceutically acceptable salts or solvates of any thereof.

Another invention embodiment is a combination, comprising naltrexone, or a pharmaceutically acceptable salt or solvate thereof, and ibuprofen, or a pharmaceutically acceptable salt or solvate thereof.

Another invention embodiment is a combination, comprising naltrexone and ibuprofen in a weight to weight combination range which corresponds to a synergistic combination range of the order of 90:1 parts by weight.

Another invention embodiment is a combination, comprising the dose range of naltrexone, or a pharmaceutically acceptable salt or solvate thereof, is about 0.004 mg/kg-0.71 mg/kg per day.

Another invention embodiment is a combination, comprising the dose range of ibuprofen, or a pharmaceutically acceptable salt or solvate thereof, is about 3 mg/kg-35 mg/kg per day.

Another invention embodiment is a combination, comprising the human dose range of naltrexone, or a pharmaceutically acceptable salt or solvate thereof, is 0.25 mg-50mg per day.

Another invention embodiment is a combination, comprising the human dose range of naltrexone, or a pharmaceutically acceptable salt or solvate thereof, is 0.25 mg-25mg per day.

Another invention embodiment is a combination, comprising the human dose range of naltrexone, or a pharmaceutically acceptable salt or solvate thereof, is 0.25 mg-15 mg per day.

Another invention embodiment is a combination, comprising the human the dose range of ibuprofen, or a pharmaceutically acceptable salt or solvate thereof, is 200 mg-2400 mg per day.

Another invention embodiment is a combination, comprising the human dose range of naltrexone, or pharmaceutically acceptable salt or solvate thereof, is 0.25 mg-50 mg per day, and the human the dose range of ibuprofen, or a pharmaceutically acceptable salt or solvate thereof, is 200 mg-2400 mg, wherein said composition is formulated into a single fixed combination dosage form.

Another invention embodiment comprising the composition is administered once, twice, three or four times through the day.

Another invention embodiment comprising the therapeutically effective dose of the pharmaceutical composition is administered systemically by such routes including but are not limited to mucosal, nasal, oral, parenteral, gastrointestinal, topical or sublingual routes.

Another invention embodiment comprising, said combination is in a single dosage form, and said single dosage form is in the form of tablets, lozenges, troches, hard candies, liquid, powders, sprays, creams, salves and suppositories.

Another invention embodiment the pharmaceutical composition is used for the treatment, prevention and reversal of neuropathic pain and inflammatory-nociceptive pain, such as inflammatory arthritic pain, back pain, chronic pain, diabetic neuropathic pain, trigeminal neuralgia pain, phantom limb pain, complex regional pain syndrome pain, acute herpetic pain, post herpetic pain, causalgia pain, idiopathic pain, inflammatory pain, cancer pain, postoperative pain, fibromyalgia pain, headache pain, migraine pain, allodynia pain, vulvodynia pain, interstitial cystitis pain, irritable bowel syndrome (IBS), arthritic joint pain and tendinitis.

Another invention embodiment is a method of treating neuropathic and nociceptive pain with an allodynic component and migraine in a mammal in need thereof, comprising administering to the mammal a therapeutically effective amount of a combination comprising an opioid/TLR4 antagonist and a cyclooxygenase inhibitor, or pharmaceutically acceptable salts or solvates of any thereof.

Another invention embodiment is a method of treating neuropathic and nociceptive pain with an allodynic component and migraine in a mammal in need thereof, comprising administering to the mammal a therapeutically effective amount of a combination comprising naltrexone and ibuprofen, or pharmaceutically acceptable salts or solvates of any thereof.

Another invention embodiment, the combination of naltrexone, or a pharmaceutically acceptable salt or solvate thereof, and ibuprofen, or a pharmaceutically acceptable salt solvate thereof, may optionally be administered with one or more other pharmacologically active agents. Appropriate optional agents include:, steroidal anti-inflammatory drugs, tricyclic antidepressants (TCAs), selective serotonin reuptake inhibitors (SSRIs), serotonin-norepinephrine reuptake inhibitors (SNRIs), anticonvulsants, muscle relaxants, drugs with NMDA antagonist properties, tetrahydrocannabinol derivatives, antitussive, expectorants, decongestants, or antihistamines.

Another invention embodiment for non-human animal administration the term "pharmaceutical" as used herein may be replaced by "veterinary".

DETAILED DESCRIPTION OF THE INVENTION

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

Pharmaceutical Composition

Naltrexone and ibuprofen were evaluated alone and in combination on a human subject with the purpose of finding whether or not a combination of the two compounds offers a synergistic advantage for the pain treatment effect comparing the amounts used weight to weight.

The components of the combination were administered to a subject as follows: the naltrexone dose administered alone was 4.5 mg, and the ibuprofen dose administered alone was 800 mg. The dose of the naltrexone/ibuprofen combination was 2.25 mg/200, respectively. The pain treatment effect was evaluated one hour post-dose.

To determine synergy, the amounts of naltrexone and ibuprofen administered alone were compared to the combination combined amounts. For proper weight to weight (W/W) comparison between naltrexone and ibuprofen an adjustment for the higher potency of naltrexone was made based on the dose of each compound given by itself. Naltrexone is 178 times more potent than ibuprofen (800/4.5=178). Naltrexone and ibuprofen were administered at fixed dose ratios of 1:90 to a human subject afflicted with neuropathic back pain.

Table 1 illustrates the naltrexone/ibuprofen ratio that exhibit weight to weight (W/W) synergy in a human subject. The 1:90 combinations represent a 2-fold lower dose of naltrexone and 4-fold lower dose of ibuprofen when administered together.

TABLE 1

Naltrexone/ibuprofen Ratios
And Weight to Weight (W/W) Synergy

| Ratio | Naltrexone mg | Ibuprofene mg | Naltrexone Potency Adjustment (×178) | % reversal of pain | Total dose Naltrexone + Adjusted ibuprofen mg | Interaction |
|---|---|---|---|---|---|---|
| 4.5:0 | 4.50 | — | 800 | 100 | 800 | — |
| 0:800 | — | 800 | | 50 | 800 | — |
| 1:90 | 2.25 | 200 | 400.00 | 100 | 200 + 400 = 600 | Synergy |

To summarize the naltrexone/ibuprofen synergistic effect, the invention teaches that the optimal contemplated naltrexone to ibuprofen combination dosage ratio is 1:90. This dosage ratio exhibits synergy of weight to weight proportion.

CITATION LIST

Bowling, Allen C. "Low-dose naltrexone (LDN) The "411" on LDN". National Multiple Sclerosis Society. Retrieved 6 Jul. 2011.

Breivik H, Borchgrevink P C, Allen S M, Rosseland L A, Romundstad L, Hals E K, Kvarstein G, Stubhaug A. Assessment of pain. Br J. Anaesth. 2008; 101(1):17-24.doi:10.1093/bja/aen103. PMID 18487245.

Eur J Neurosci TNFα Levels and Macrophages Expression Reflect an Inflammatory Potential of Trigeminal Ganglia in a Mouse Model of Familial Hemiplegic Migraine Nat Rev Neurosci. 2009 January; 10(1): 23-36.

Hutchinson M R, Coats B D, Lewis S S, Zhang Y, Sprunger D B, Rezvani N, Baker E M, Jekich B M, Wieseler J L, Somogyi A A, Martin D, Poole S, Judd C M, Maier S F, Watkins L R (November 2008). "Proinflammatory cytokines oppose opioid induced acute and chronic analgesia". Brain, Behavior, and Immunity 22 (8): 1178-89. doi:10.1016/j.bbi.2008.05.004. PMC 2783238.PMID 18599265.

Hutchinson M R, Lewis S S, Coats B D, Rezvani N, Zhang Y, Wieseler J L, Somogyi A A, Yin H, Maier S F, Rice K C, Watkins L R (May 2010). "Possible involvement of Toll-Like Receptor 4/MD-2 activity of opioid inactive isomers causes spinal proinflammation and related behavioral consequences". Neuroscience 167 (3): 880-93. doi:10.1016/j.neuroscience.2010.02.011.PMC 2854318. PMID 20178837.

Hutchinson M R, et al. Opioid-induced glial activation: mechanisms of activation and implications for opioid analgesia, dependence and reward. Sci. World J. 2007; 7:98-111.

Hutchinson M R, et al. Non-stereoselective reversal of neuropathic pain by naloxone and naltrexone: involvement of toll-like receptor 4 (TLR4) Eur. J. Neurosci. 2008; 28:20-.

Hutchinson M R, Lewis S S, Coats B D, Rezvani N, Zhang Y, Wieseler J L, Somogyi A A, Yin H, Maier S F, Rice K C, Watkins L R (May 2010). "Possible involvement of Toll-Like Receptor 4/MD-2 activity of opioid inactive isomers causes spinal proinflammation and related behavioral consequences". Neuroscience 167 (3): 880-93.doi:10.1016/j.neuroscience.2010.02.011. PMC 2854318. PMID 20178837.

Hutchinson M R, et al. Proinflammatory cytokines oppose opioid-induced acute and chronic analgesia. Brain Behav. Immun. 2008 Jul. 1.

Hutchinson M R, et al. Minocycline supresses morphine-induced respiratory depression, supresses morphine-induced reward, and enhances systemic morphine-induced analgesia. Brain Behav. Immun. 2008 Jul. 31.

Johnston I N, et al. A role for pro-inflammatory cytokines and fractalkine in analgesia, tolerance and subsequent pain facilitation induced by chronic intrathecal morphine. 2004; 24:7353-7365.

Komatsu T, Sakurada S, Katsuyama S, Sanai K, Sakurada T (2009). "Mechanism of allodynia evoked by intrathecal morphine-3-glucuronide in mice". International Review of Neurobiology 85: 207-19. doi:10.1016/50074-7742(09)85016-2.PMID 19607972.

Lewis S S, Hutchinson M R, Rezvani N, Loram L C, Zhang Y, Maier S F, Rice K C, Watkins L R (January 2010). "Evidence that intrathecal morphine-3-glucuronide may cause pain enhancement via toll-like receptor 4/MD-2 and interleukin-1β". Neuroscience 165 (2): 569-83. doi: 10.1016/j.neuroscience.2009.10.011.PMC 2795035. PMID 19833175.

Mannelli P, Gottheil E, Van Bockstaele E J (2006). "Antagonist treatment of opioid withdrawal translational low dose approach". J Addict Dis 25 (2): 1-8.doi: 10.1300/J069v25n02_01. PMID 16785213.

Milligan, E. D., and Watkins, L. R., Pathological and protective roles of glia in chronic pain, Nature Neuroscience Reviews, 10 (2009) 23-36.

Nasu-Tada K, Koizumi S, Tsuda M, Kunifusa E, Inoue K. Possible involvement of increase in spinal fibronectin following peripheral nerve injury in upregulation of microglial P2×4, a key molecule for mechanical allodynia. Glia. 2006; 53:769-775.

Ngian G S, Guymer E K, Littlejohn G O (February 2011). "The use of opioids in fibromyalgia" (PDF). Int J Rheum Dis 14 (1): 6-11. doi:10.1111/j.1756-185X.2010.01567.x. PMID 21303476.

Novella, Steven. "Low Dose Naltrexone—Bogus or Cutting Edge Science?". Retrieved 5 Jul. 2011.

Obata K, et al. Toll-like receptor 3 contributes to spinal glial activation and tactile allodynia after nerve injury. J. Neurochem. 2008; 105:2249-2259.

Romero-Sandoval E A, Horvath R J, Deleo J A. Neuroimmune interactions and pain: focus on glial modulating targets. Curr. Opin. Investig. Drugs. 2008; 9:726-734.

Ploesser J, Weinstock L B, Thomas E. Low Dose Naltrexone: Side Effects and Efficacy in Gastrointestinal Disorders.

Tanga F Y, Nutile-McMenemy N, DeLeo J A. The CNS role of Toll-like receptor 4 in innate neuroimmunity and painful neuropathy. Proc. Natl Acad. Sci. USA. 2005; 102:5856-5861.

Turk D C, Dworkin R H. What should be the core outcomes in chronic pain clinical trials?. Arthritis Res. Ther. 2004; 6(4):151-4. doi:10.1186/ar1196. PMID 15225358.

Watkins L R, Hutchinson M R, Rice K C, Maier S F (November 2009). "The

"Toll" of Opioid-Induced Glial Activation: Improving the Clinical Efficacy of Opioids by Targeting Glia". Trends in Pharmacological Sciences 30 (11): 581-91. doi:10.1016/j.tips.2009.08.002. PMC 2783351.PMID 19762094.

Webster L R (August 2007). "Oxytrex: an oxycodone and ultra-low-dose naltrexone formulation". Expert Opin Investig Drugs 16 (8): 1277-83.doi:10.1517/13543784.16.8.1277. PMID 17685875.

That which is claimed is:

1. A composition for treatment of pain in a mammal comprising physiologically active agents, wherein any physiologically active agents in the composition consist of a synergistic ratio of naltrexone, or pharmaceutically acceptable salts or solvates thereof, and ibuprofen, or pharmaceutically acceptable salts or solvates thereof, wherein naltrexone is present in a dose range of 0.25 mg-50 mg per day, and ibuprofen is present in a dose range of 200 mg-2400 mg per day, wherein the composition is formulated into a single fixed combination dosage form.

2. The composition of claim 1, wherein the naltrexone or pharmaceutically acceptable salt or solvate thereof is in a sustained release formulation.

3. The composition of claim 1, wherein the naltrexone or pharmaceutically acceptable salt or solvate thereof is (+)-naltrexone (dextro-naltrexone), or pharmaceutically acceptable salts or solvates thereof.

4. The composition of claim 1, wherein naltrexone and ibuprofen, or pharmaceutically acceptable salts or solvates thereof, are in a a synergistic ratio of 1:90 parts by weight.

5. The composition of claim 4, wherein the dose range of naltrexone, or pharmaceutically acceptable salts or solvates thereof, is about 0.004 mg/kg-0.71 mg/kg per day, and wherein the dose range of ibuprofen, or pharmaceutically acceptable salts or solvates thereof, is about 3 mg/kg-35 mg/kg per day.

6. The composition of claim 4, wherein the dose range of naltrexone is 0.25 mg-15 mg per day, and wherein the dose range of ibuprofen is 200 mg-2400mg per day.

7. The composition of claim 4, wherein the composition is administered once, twice, three or four times throughout the day.

8. The composition of claim 4, wherein the therapeutically effective dose of the pharmaceutical composition is administered systemically, including but not limited to mucosal, nasal, oral, parenteral, gastrointestinal, topical or sublingual routes.

9. The composition of claim 4, wherein said combination is in a single dosage form, and wherein said single dosage form is in the form of tablets, lozenges, troches, hard candies, liquid, powders, sprays, creams, salves or suppositories.

* * * * *